(12) United States Patent
Machata et al.

(10) Patent No.: US 9,707,056 B2
(45) Date of Patent: Jul. 18, 2017

(54) INDIRECT BONDING TRAY AND METHOD OF MANUFACTURE THEREOF

(71) Applicant: American Orthodontics Corporation, Sheboygan, WI (US)

(72) Inventors: William Charles Machata, Kohler, WI (US); Michael Craig Marshall, Sheboygan Falls, WI (US)

(73) Assignee: American Orthodontics Corporation, Sheboygan, WI (US)

( * ) Notice: Subject to any disclaimer, the term of this patent is extended or adjusted under 35 U.S.C. 154(b) by 584 days.

(21) Appl. No.: 14/199,343

(22) Filed: Mar. 6, 2014

(65) Prior Publication Data

US 2014/0255864 A1  Sep. 11, 2014

Related U.S. Application Data

(60) Provisional application No. 61/773,404, filed on Mar. 6, 2013.

(51) Int. Cl.
*A61C 7/14* (2006.01)
(52) U.S. Cl.
CPC .................................. *A61C 7/146* (2013.01)
(58) Field of Classification Search
CPC .......................................................... A61B 17/146
USPC ..................................... 433/3, 9, 16, 24, 229
See application file for complete search history.

(56) References Cited

U.S. PATENT DOCUMENTS

| | | | |
|---|---|---|---|
| 3,738,005 A | 6/1973 | Cohen et al. | |
| 4,014,096 A | 3/1977 | Dellinger | |
| 4,117,596 A | 10/1978 | Wallshein | |
| 4,455,138 A | 6/1984 | Sheridan | |
| 4,501,554 A | 2/1985 | Hickham | |

(Continued)

FOREIGN PATENT DOCUMENTS

| | | |
|---|---|---|
| EP | 1494607 B1 | 1/2009 |
| WO | 2007069881 A1 | 6/2007 |

(Continued)

OTHER PUBLICATIONS

Cha, Bong-Kuen, "Clinical Application of Three-Dimensional Reverse Engineering Technology in Orthodontic Diagnosis", Principles in Contemporary Orthodontics, Dr. Silvano Naretto (Ed.), http://www.intechopen.com/books/principles-in-contemporaryorthodontics/clinical-application-of-three-dimensional-reverse-engineering-technology-in-orthodontic-diagnosis, 2011.

(Continued)

*Primary Examiner* — Pedro Philogene
*Assistant Examiner* — David C Comstock
(74) *Attorney, Agent, or Firm* — Andrus Intellectual Property Law, LLP

(57) ABSTRACT

An indirect bonding tray includes a least on tooth position each tooth portion includes an occlusal surface that conforms to an occlusal surface of an associated tooth of a patient's dentition. At least one of bracket arm includes a bracket arm tip configured to engage an orthodontic bracket. The at least one bracket arm movably attached to at least one tooth portion to move between a first position and second position relative to a bonding surface of the associated tooth. In the second position, the bracket arm is in a position configured to hold an orthodontic bracket in a predetermined treatment position relative to the bonding surface of the associated tooth.

20 Claims, 4 Drawing Sheets

(56) References Cited

U.S. PATENT DOCUMENTS

| | | | |
|---|---|---|---|
| 4,551,096 A | 11/1985 | Dellinger | |
| 4,626,208 A * | 12/1986 | Hall | G01S 13/755 433/3 |
| 4,657,508 A | 4/1987 | Dellinger | |
| 5,055,038 A * | 10/1991 | Ronay | A61C 7/146 433/24 |
| 5,542,842 A | 8/1996 | Andreiko et al. | |
| 5,791,896 A | 8/1998 | Ipenburg | |
| 5,863,198 A | 1/1999 | Doyle | |
| 5,879,158 A | 3/1999 | Doyle et al. | |
| 5,971,754 A | 10/1999 | Sondhi et al. | |
| 6,086,855 A | 7/2000 | Fischer | |
| 6,123,544 A | 9/2000 | Cleary | |
| 6,293,790 B1 | 9/2001 | Hilliard | |
| 6,554,613 B1 | 4/2003 | Sachdeva et al. | |
| 6,607,382 B1 | 8/2003 | Kuo et al. | |
| 6,702,575 B2 | 3/2004 | Hilliard | |
| 6,905,337 B1 | 6/2005 | Sachdeva | |
| 7,056,115 B2 | 6/2006 | Phan et al. | |
| 7,077,646 B2 | 7/2006 | Hilliard | |
| 7,094,053 B2 | 8/2006 | Andreiko et al. | |
| 7,125,248 B2 | 10/2006 | Phan et al. | |
| 7,252,509 B2 | 8/2007 | Sachdeva | |
| 7,347,688 B2 | 3/2008 | Kopelman et al. | |
| 7,410,357 B2 | 8/2008 | Cleary et al. | |
| 7,578,673 B2 | 8/2009 | Wen et al. | |
| 7,600,999 B2 | 10/2009 | Knopp | |
| 7,658,610 B2 | 2/2010 | Knopp | |
| 7,690,917 B2 | 4/2010 | Marshall | |
| 7,762,815 B2 | 7/2010 | Cinader, Jr. et al. | |
| 7,845,938 B2 | 12/2010 | Kim et al. | |
| 7,905,724 B2 | 3/2011 | Kuo et al. | |
| 7,950,131 B2 | 5/2011 | Hilliard | |
| 8,002,543 B2 | 8/2011 | Kang et al. | |
| 8,060,236 B2 | 11/2011 | Hilliard | |
| 8,235,715 B2 | 8/2012 | Kuo | |
| 8,401,686 B2 | 3/2013 | Moss et al. | |
| 8,496,473 B2 | 7/2013 | Phan et al. | |
| 2004/0166462 A1 | 8/2004 | Phan et al. | |
| 2007/0111154 A1 | 5/2007 | Sampermans | |
| 2010/0159412 A1 | 6/2010 | Moss et al. | |
| 2010/0216083 A1 | 8/2010 | Grobbee | |
| 2011/0250556 A1 | 10/2011 | Heiser | |
| 2012/0150494 A1 | 6/2012 | Anderson et al. | |
| 2013/0095448 A1 | 4/2013 | Phan et al. | |
| 2013/0196279 A1 | 8/2013 | Curiel | |

FOREIGN PATENT DOCUMENTS

| | | |
|---|---|---|
| WO | 2009056776 A2 | 5/2009 |
| WO | 2011022654 A1 | 2/2011 |

OTHER PUBLICATIONS

Come Fixes, Advanced IDBS System Benefits Approval by Dental Arirang, http://m.dentalarirang.com/news/articleView.html?idxno=8807, website visited on Dec. 15, 2015.
Great Smile made by Orapix brochure, dated Jun. 3, 2013.
Kieferorthorädie Nachrichten, No. 5, May 2011.
Kieferorthorädie Nachrichten, No. 12, Dec. 2014.
Specialty Appliances Indirect Bonding (IB) Reference Manual, 2012.

* cited by examiner

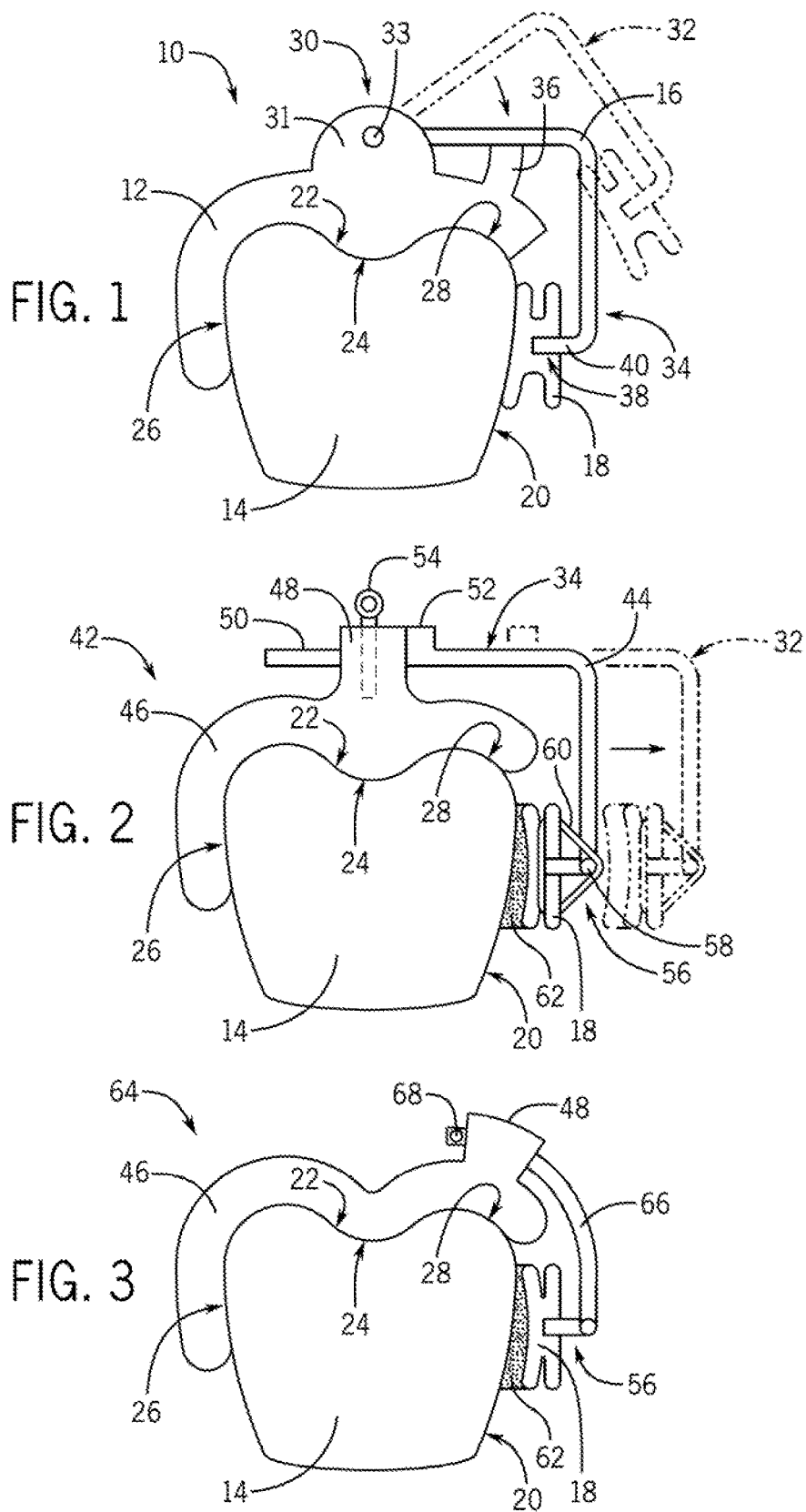

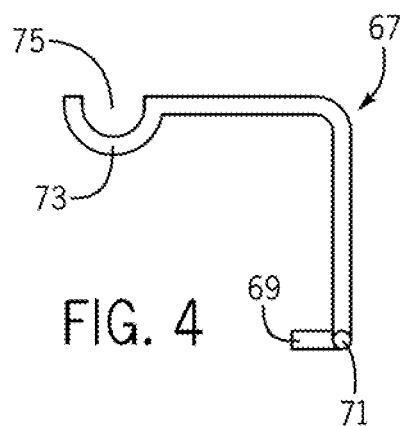
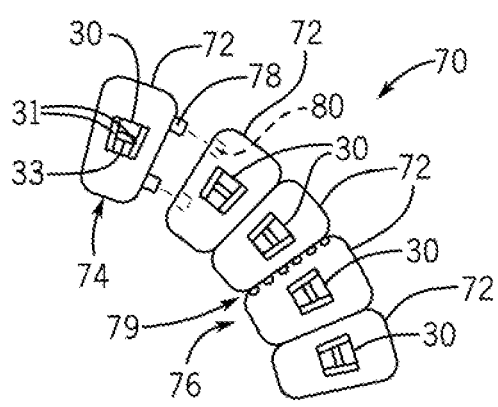
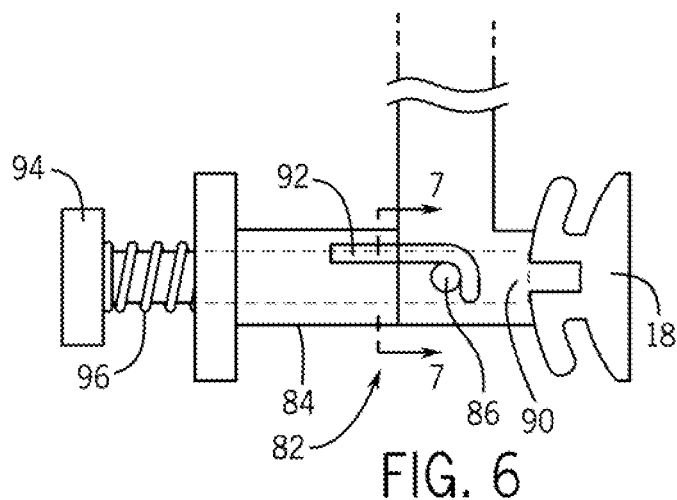
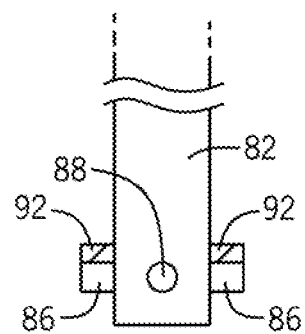

INDIRECT BONDING TRAY AND METHOD OF MANUFACTURE THEREOF

CROSS-REFERENCE TO RELATED APPLICATION

The present application claims priority of U.S. Provisional Patent Application No. 61/773,404, filed on Mar. 6, 2013, the content of which is hereby incorporated herein by reference in its entirety.

BACKGROUND

The present disclosure relates to the field of orthodontics. More specifically, the present disclosure relates to a tray for use in an indirect bonding method of orthodontic bracket application, and a method of manufacturing such a tray.

Orthodontic brackets can be bonded to a patient's teeth by an orthodontist either through a direct method in which the orthodontist manually bonds each bracket one at a time to each of the patient's teeth or through an indirect method in which a bonding tray holds and seats multiple brackets to the patient's teeth. While the indirect bonding technique offers some alignment verification through the use of the tray, bracket placement through either manual or indirect bonding techniques is determined by experience and skill of the orthodontist. Incorrect bracket placement often leads to unintended arch wire bending or the need for bracket repositioning during treatment. These intra-treatment procedures are time consuming clinically and can lead to prolonged treatment times.

Available indirect bonding trays also generally limit access to bracket pads during the bonding process which can present challenges for orthodontists to create clean and reliable bonds on all of the brackets applied to a patient's teeth.

BRIEF DISCLOSURE

An exemplary embodiment of an indirect bonding tray includes a tray that includes a plurality of tooth portions. Each tooth portion of the tray includes an occlusal surface that conforms to an occlusal surface of an associated tooth of a patient's dentition. A plurality of bracket arms each include a bracket arm tip that is configured to engage an orthodontic bracket. Each bracket arm is moveably attached to one of the plurality of tooth portions. Each bracket arm is individually dimensioned to move between a first position and a second position relative to a bonding surface of the associated tooth. In the first position the bracket arm tip is in a position away from the associated tooth. In the second position the bracket arm is in a position configured to hold an orthodontic bracket in a predetermined treatment position relative to the bonding surface of the associated tooth.

An exemplary embodiment of an indirect bonding tray system includes a first tooth portion that includes an occlusal surface that conforms to an occlusal surface of a first specific tooth of a patient's dentition. The first tooth portion includes a second surface that conforms to a surface of the first specific tooth opposite a bonding surface of the first specific tooth. A first bracket arm includes a bracket arm tip. The first bracket arm is moveably attached to the tooth portion to move between a first position and a second position. A first orthodontic bracket is configured to engage the bracket arm tip. The first bracket arm is digitally designed relative to a predetermined idealized bracket placement for the first specific tooth such that the first bracket arm is dimensioned to hold the first orthodontic bracket in the predetermined idealized bracket placement relative to the bonding surface of the first specific tooth when the first bracket arm in the second position.

An additional exemplary embodiment of an indirect bonding tray system includes a first tooth portion that includes an occlusal surface that conforms to an occlusal surface of a first specific tooth of a patient's dentition. The first tooth portion includes a second surface that conforms to a surface of the first specific tooth opposite a bonding surface of the first specific tooth. A first bracket arm includes a bracket arm tip configured to engage a first orthodontic bracket. The first bracket arm is moveably attached to the tooth portion to move between a first position and a second position. The first bracket arm is digitally designed relative to a predetermined idealized bracket placement for the first specific tooth such that the first bracket arm is dimensioned to hold the first orthodontic bracket in the predetermined idealized bracket placement relative to the bonding surface of a first specific tooth when the first bracket arm is in the second position. A first stop mechanically defines the second position of a first bracket arm relative to the first tooth portion. A second tooth portion is removably secured to the first tooth portion. The second tooth portion includes an occlusal surface that conforms to an occlusal surface of a second specific tooth of the patient's dentition. The second tooth portion further includes a second surface that conforms to a surface of the second specific tooth opposite a binding surface of the second specific tooth. A second bracket arm includes a bracket arm tip configured to engage the second orthodontic bracket. The second bracket arm is moveably attached to the second tooth portion to move between a first position and a second position. The second bracket arm is digitally designed relative to a predetermined idealized bracket placement for the second specific tooth such that the second bracket arm is dimensioned to hold the second orthodontic bracket in the predetermined idealized bracket placement relative to the bonding surface of the second specific tooth when the second bracket arm is in the second position. A second stop mechanically defines the second position of the second bracket arm relative to the second tooth portion.

BRIEF DESCRIPTION OF THE DRAWINGS

FIG. 1 is a cross-sectional view of an embodiment of an indirect bonding tray with a pivoting arm.

FIG. 2 is a cross-sectional view of an embodiment of an indirect bonding tray with a sliding arm.

FIG. 3 is a cross-sectional view of an alternative embodiment of an indirect bonding tray with a sliding arm.

FIG. 4 is a side view depicting an exemplary embodiment of an arm for use with an indirect bonding tray.

FIG. 5 is a top view depicting an embodiment of a segmented indirect bonding tray.

FIG. 6 depicts an embodiment of an arm and bracket in conjunction with a releasing device.

FIG. 7 depicts a front view of the arm taken along line 7-7 in FIG. 6.

DETAILED DISCLOSURE

Indirect bonding trays as disclosed herein and the methods of manufacturing such trays can be used by dental professionals to precisely place orthodontic brackets and/or create customized composite bases for orthodontic brackets placed in a direct or indirect manner.

Figure 8:
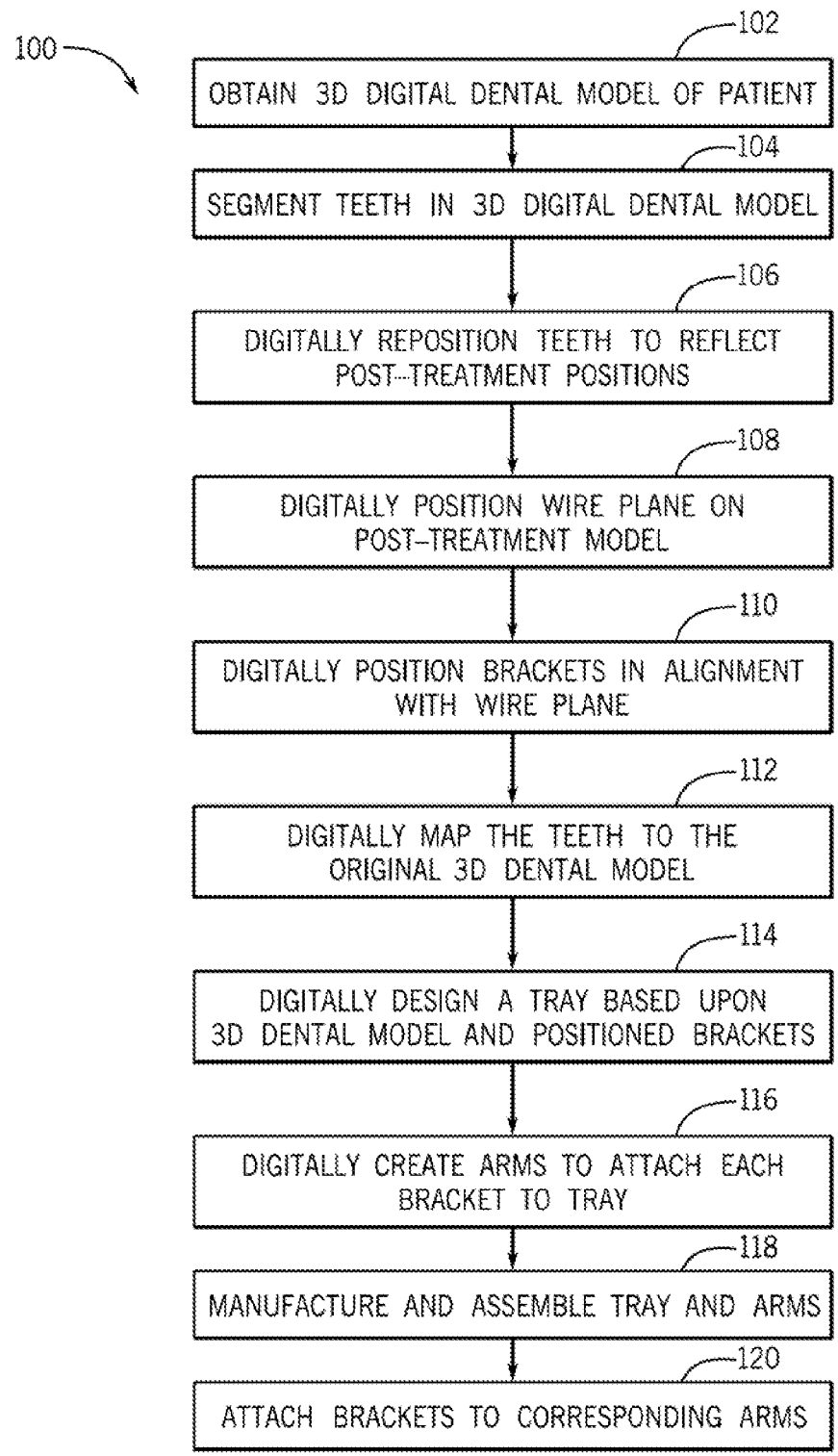
FIG. 8 is a flow chart that depicts an embodiment of a method of fabricating an indirect bonding tray.

FIGS. 1-7, as will be described in greater detail herein, present various embodiments of indirect bonding trays which in some embodiments may be constructed according to the method as disclosed herein with respect to FIG. 8. Still further embodiments of indirect bonding trays may be used in accordance with the method 200 of using an indirect bonding tray to construct customized composite bases depicted in the flow chart of FIG. 9. FIG. 8 is a flow chart that depicts an embodiment of a method 100 of manufacturing an indirect bonding tray. At 102 a three-dimensional digital model of the patient's pre-treatment dentition is obtained. This 3D digital model may be obtained in a variety of ways including, but not limited to medical imaging techniques such as computed tomography (CT), by creating a plaster cast of the patient's dentition and digitally scanning the cast, or by intraoral scanning.

At 104 the 3-D digital model is manipulated to segment the individual teeth within the 3-D digital model. The separated teeth are digitally repositioned at 106 to reflect the desired post-treatment positions of the patient's teeth. Each of the transformations required to digitally reposition the separated teeth are recorded and saved. This creates both a record of the original pre-treatment dentition and the transformation required by treatment. Once the teeth have been repositioned into the post-treatment positions at 108, an arch wire plane is positioned on the post-treatment model created at 106. It is to be noted that in embodiments, the arch wire plane may be curved, exemplarily to reflect curve of Spee, curve of Wilson, or other dentition.

At 110 distal brackets are digitally positioned on each of the patient's teeth in alignment with the arch wire plane. The brackets are positioned such that a slot in each bracket coincides with the wire plane and the bracket pad is touching or nearly touching the appropriate surfaces of the teeth in the post-treatment model. Once the individual relationship between each of the brackets and the teeth in the post-treatment model has been established, at 112 the positioned brackets are mapped back to the original 3-D digital model of the patient's pre-treatment dentition. This mapping may be carried out by reversing each of the previously recorded and stored transformations to digitally reposition the teeth.

At 114 a bonding tray is digitally designed around the 3-D digital model of the patient's dentition and the positioned brackets. The tray may be any of the trays as disclosed in further detail herein, and is designed to conform to the appropriate tooth surfaces such that the tray conforms to the dentition while not interfering with the placement of the brackets on the patient's teeth. Exemplarily, the tray may be designed to conform to the occlusal tooth surface and if the brackets are placed on the labial tooth surface, then the tray is designed to conform to the opposite lingual tooth surfaces. On the other hand, if the brackets are to be placed lingually, then the tray is designed to conform to the labial tooth surfaces. It is to be recognized that in further embodiments, a combination of bracket placement and conforming tooth surfaces of the tray may be used in a single tray. The digital design of the tray may be performed automatedly with the application of standard tray dimensions relative to the 3-D digital model of the patient's dentition. Alternatively, a technician may input one or more boundaries or parameters for the design of the tray or select from one or more basic tray templates and the additional features of the tray can be added automatically based upon the 3-D digital model and the bracket placements.

At 116 bracket arms are digitally created to movably attach each bracket to the tray. The bracket arms may exemplarily be any of the bracket arms as described in embodiments in further detail herein. The bracket arms are designed to move with respect to the tray and end movement at the digitally located bracket position. The design of the bracket arms may be performed automatedly by applying predefined algorithms or design relationships that define the size, shape, and/or dimensions of the bracket arms to the digitally created tray and the bracket placements. The bracket arm design may be done automatedly or upon a technician selection of a particular bracket arm design or configuration. The bracket arms are designed with relationship to the position of the bracket on the tooth and the portion of the tray designed to conform with that tooth. Embodiments of the bracket arms may be designed with bracket arm tips that are dimensioned to fit an arch wire slot or another physical feature of a corresponding bracket. The bracket arm tip may be dimensioned to provide a friction fit with the bracket or another physical feature of the bracket. Additionally, the bracket arm design and/or bracket arm tip design cooperates with the physical features of the bracket to position the bracket at the predetermined torque, tilt, or rotation relative to the tooth.

At 118 the digitally designed tray and bracket arms are manufactured. The manufacture of such a digitally designed tray and bracket arms may be done exemplarily through 3-D printing or computer assisted milling. However, it is understood that other manufacturing techniques may be used. In embodiments in which the tray and bracket arms are not manufactured in a pre-assembled form, the trays and bracket arm are then assembled. In some embodiments, it is recognized that the bracket arms may be movably fixed to the tray. While in other embodiments, the bracket arms may be removable from connection with the tray. At 120 the brackets to be bonded to the patient's teeth are attached to the corresponding bracket arms.

Referring to FIG. 1, FIG. 1 depicts a cross sectional view of an exemplary embodiment of an indirect bonding tray 10 as may be constructed in accordance with the method disclosed herein. The indirect bonding tray 10 includes a tray 12 that is designed to conform to a patient's tooth 14 and a bracket arm 16 that is configured to movably position an orthodontic bracket 18 with respect to a bonding surface 20 of the tooth 14. It will be recognized that in embodiments, the indirect bonding tray 10 is configured to assist in the placement of a plurality of brackets to a plurality of teeth in a patient's dentition.

As described above, the tray 12 is designed to conform to one or more surfaces of the tooth. Namely, the tray 12 includes an occlusal surface 22 to conform to an occlusal surface 24 of the tooth 14. The tray 12 can also include a second surface 26 that is configured to conform to one of the tooth sides, namely a lingual side or a labial side of the tooth 14. It is to be recognized that the tooth 14 depicted in FIG. 1 is generically depicted such that either side of the tooth may represent the lingual or labial side. In still further embodiments, the tray 12 may include a third surface 28 which is configured to conform to at least a portion of the bonding surface 20 of the tooth 14 while leaving the area about the bracket 18 and the bonding surface 20 to which the bracket 18 will be secured open and free of obstruction. It is to be understood that the bonding surface 20 is the other of the lingual or labial side of the tooth that is not engaged by the second surface 26 of the tray 12.

As previously disclosed, the bracket arm 16 is movably secured to the tray 12. In the embodiment of the indirect bonding tray depicted in FIG. 1, the bracket arm 16 is pivotally connected to the tray 12 at a pivot 30. Further as previously disclosed, the bracket arm 16 is designed to move between a first position wherein the bracket arm and attached bracket 18 are pivoted away from the bonding surface 20 as depicted in dashed lines at reference number 32. The bracket arm 16 rotates to a second position 34 wherein the bracket 18 engages, or, as described in further detail herein, is held in close proximity to the bonding surface 20 of the tooth 14 at the position digitally determined for proper bracket placement. The bracket arm 16 further holds the bracket 18, in the second position 34, at a determined torque, tilt, or rotation required for proper placement of the bracket 18. Embodiments of the tray 12 may include a physical stop 36 that defines the second position 34 of the movable bracket arm 16 by preventing further bracket arm movement beyond the second position 34.

The bracket 18 includes an arch wire slot 38 and the bracket arm 16 has a tip 40 configured to engage the arch wire slot 38. As depicted in FIG. 1, the tip 40 may engage the arch wire slot 38 in a friction fit engagement; however, other embodiments as described herein may include alternative engagements. It is to be noted that brackets 18 may include one or more slots, or a particular orientation of the slot or slots. The tip 40 of the bracket arm may be configured to engage the specific design of the slots in the bracket 18. Such configurations of the tip may be digitally designed relative to the specific brackets predetermined for orthodontic treatment of the patient. In further embodiments, a plurality of arms may each have differently shaped tips to accommodate the specific bracket prescribed to the tooth to which the tray position and arm are associated.

FIG. 2 depicts an alternative embodiment of an indirect bonding tray 42. It is to be noted that like reference numerals are used herein to represent like features for purposes of preciseness and in order to focus on particular features as described herein.

The bracket arm 44 depicted in FIG. 2 is movably connected to the tray 46 in a slidable manner such that the bracket arm 44 moves the bracket 18 towards and away from the bonding surface 20 of the tooth 14 between a first position 32 and a second position 34. The tray 46 is configured with an aperture or guide 48 that is configured to receive a sliding portion 50 of the bracket arm 44 such that the bracket arm 44 can translate with respect to the tooth 14 and the tray 46. A stop 52 on the bracket arm 44 engages the guide 48 structure in order to define the second position 34 of the bracket arm 44 in the digitally configured proper placement of the bracket 18 in relation to the bonding surface 20. In some embodiments, a pin 54 may also be used to fixedly secure the bracket arm 44 in the second position 34 in order to facilitate bonding of the bracket 18 to the patient's tooth. In an example, this bonding may occur by holding the bracket in the desired second position relative to the patient's tooth while the orthodontist cleans any excess flash from the bracket and bonding surface of the tooth before the composite and/or bonding material is cured.

FIG. 2 also depicts an alternative embodiment of the bracket arm tip 56. In such an embodiment, the bracket arm tip 56 further includes one or more pins 58 that extend from the bracket arm 44. An elastic band 60 engages both the one or more pins 58 and exemplary tie wings of the bracket 18 in order to releasably secure the bracket 18 to the bracket arm 44. This method of securing the bracket arm tip 56 to the bracket 18 may be used in conjunction with or instead of the previously discussed friction fit engagement between the bracket 18 and the bracket arm tip 56.

As will be described in further detail herein, in some embodiments, the bracket 18 may be customized with an additional composite base 62 on the bracket pad that is designed to fill any gap between the pad of the digitally positioned bracket 18 and the treatment surface 20 of the patient's tooth 14. The composite base 62 can thus facilitate a customized fit specifically configured to conform to a bonding surface 20 of the patient's tooth 14. Such use of a composite base may facilitate the use of a less complexly bended arch wire or may reduce or eliminate the need to custom manufacture brackets specific to the patient, composite bases may also be used to impart a torque and/or a rotation on the tooth 14.

FIG. 3 is a side-view depiction of a still further embodiment of an indirect bonding tray 64 in which the bracket arm 66 is curved and slidably engages the guide 48 on the tray 46 in a curved manner. The guide 48 defines a movement path of the bracket arm 66 such that when the bracket arm 66 is in the first position (not depicted), the bracket 18 is rotated away from the treatment surface. A stop 68 on the bracket arm engages the guide 48 to precisely define and hold the bracket 18 and bracket arm 66 in the second position.

FIG. 4 is a side view depicting an exemplary alternative embodiment of a bracket arm 67 for use with embodiments of an indirect bonding tray as disclosed herein. The bracket arm 67 is configured to removably and pivotally engage a pivot 30. A top view of a merely exemplary embodiment of a pivot 30 is depicted in FIG. 5. The pivot 30 of FIG. 5 may exemplarily be the same pivot 30 as depicted in FIG. 1. The pivot 30 exemplarily includes pivot sides 31 and a pivot pin 33. It will be appreciated that in alternative embodiments, the pivot 30 may include only a single pivot side 31 which would facilitate receipt of a bracket arm by sliding over an open end of the pivot pin 33. In another embodiment, the pivot 30 may be arranged with a vertically oriented pivot pin, exemplarily to facilitate rotational pivoting of a bracket arm.

Referring back to FIG. 4, the bracket arm 67 includes an arm tip 69 configured to engage a bracket (not depicted) and exemplarily including one or more pins 71 as described above with respect to FIG. 2 operable to further secure the bracket to the arm 67. The bracket arm 67 further includes a rotation finger 73 that is shaped to form a rotation cavity 75 configured to removably and pivotally receive the pivot pin 33 of the pivot 30. In embodiments, the rotation finger 73 may be dimensioned such as to removably receive the pivot pin, but also to retain engagement of the pivot pin with the rotation cavity 75 as the bracket arm is moved between both the first and second positions.

In a still further embodiment, the bracket arm may include a ring or annulus (not depicted) configured to receive the pivot pin. Such a bracket arm may exemplarily be configured similarly to that described with respect to FIG. 1, although when used in conjunction with a pivot that includes a single pivot side 31, facilitates the removable engagement with the pivot by slidably receiving the pivot pin within the annulus.

FIG. 5 is an occlusal view of a partial embodiment of an indirect bonding tray 70 wherein the indirect bonding tray 70 is constructed in the manner as described above with respect to FIG. 1, including the pivot 30. For the sake of clarity, the bracket arms are not depicted in FIG. 5; however, it is to be recognized that in embodiments, bracket arms would also be included. The bracket arms may exemplarily be integral components as depicted with respect to FIG. 1, or may be removable bracket arms as depicted in FIG. 4.

Still further embodiments may be implements in the sliding configurations of FIGS. 2 and 3, or any other disclosed embodiments as recognized in view of the current disclosure. The indirect bonding tray 70 depicted in FIG. 4 shows that in some embodiments, a full or partial arch of an indirect bonding tray can be formed by a plurality of tooth portions 72 that are designed to conform to either a single tooth as a single tooth portion 74 or to a group of teeth as groups 76 of tooth portions. In an embodiment, the groups 76 of tooth portions may be constructed as a unitary or separated/separable construction. It will be understood that in embodiments, any combination of single tooth portions 74 and/or groups 76 of tooth portions may be used to create an indirect bonding tray 70 that corresponds to a full or partial arch of a patient's dentition. In still further embodiments, a partial tray may be similarly formed in order to place brackets on only a portion of a patient's dentition. Tooth portions 72 can be configured to releasably attach to one another in order to form an indirect bonding tray 70, exemplarily through the use of mating a tab 78 with a slot 80. In an embodiment, each tooth portion 72 includes a set of tabs 78 and slots 80, such that adjacent tooth portions 72 are connectable. In still further embodiments, groups 76 of tooth portions 72 are connectable by similarly mating tabs 78 and slots 80. In an alternative embodiment, the bonding tray 70 may be formed as a unitary construction covering the dentition of an arch or a partial arch and individual teeth and/or portions of teeth of the indirect bonding tray 70 separated by perforations 79 that facilitate separation of the indirect bonding tray 70 into smaller segments. In an embodiment, each tooth portion 72 may be separable by perforations 79, while in other embodiments, perforations separate groups of tooth portions 72.

FIG. 6 depicts an alternative embodiment of a bracket arm tip 82 that may be used in conjunction with a release plunger 84 or other similarly constructed device. FIG. 7 is a front view taken along line 7-7 in FIG. 6. FIGS. 6 and 7 show pins 86 extending outwardly from the bracket arm tip 82. A through hole 88 through the bracket arm tip 82 is configured to receive a release arm 90 of the release plunger 84. The bracket arm tip 82 is configured to releasably secure to the bracket 18 in one of the manners as described above, or alternatively, with the use of a mild adhesive. After a bracket 18 is bonded to the treatment surface of a patient's tooth, disengagement between the bracket arm tip 82 and the bracket 18 can place undesired force on the newly created bond. Therefore, in order to reduce this force placed on the new bond between the bracket and the tooth, the release plunger 84 engages the bracket arm tip 82 and the movable release arm 90 moves through the through hole 88 in the bracket arm tip 82 to engage the bracket 18 while one or more hooks 92 of the release plunger 84 engage the pins 86. In an embodiment, the hooks 92 are pivotable or resiliently moveable to facilitate engagement and disengagement of the hooks 92 from the pins 86. When a button 94 of the release plunger 84 is depressed, the release arm 90 places a separating force between the bracket 18 and the bracket arm tip 82 in order to remove the bracket arm tip 82 from the bracket 18 with limited force applied to the newly formed bond between the bracket and the tooth. In some embodiments, the release plunger 84 may include a spring 96 or other biasing device that holds the button 94 in the non-engaged position to facilitate entry and removal of the release arm 90 in the through hole 88.

As described above, and particularly with reference to FIGS. 2 and 3, embodiments of the indirect bonding tray as described herein can include a custom composite base 62 applied to each of the brackets 18 in order to provide an individualized fit between the brackets and the treatment surface of the patient's teeth.

Figure 9:
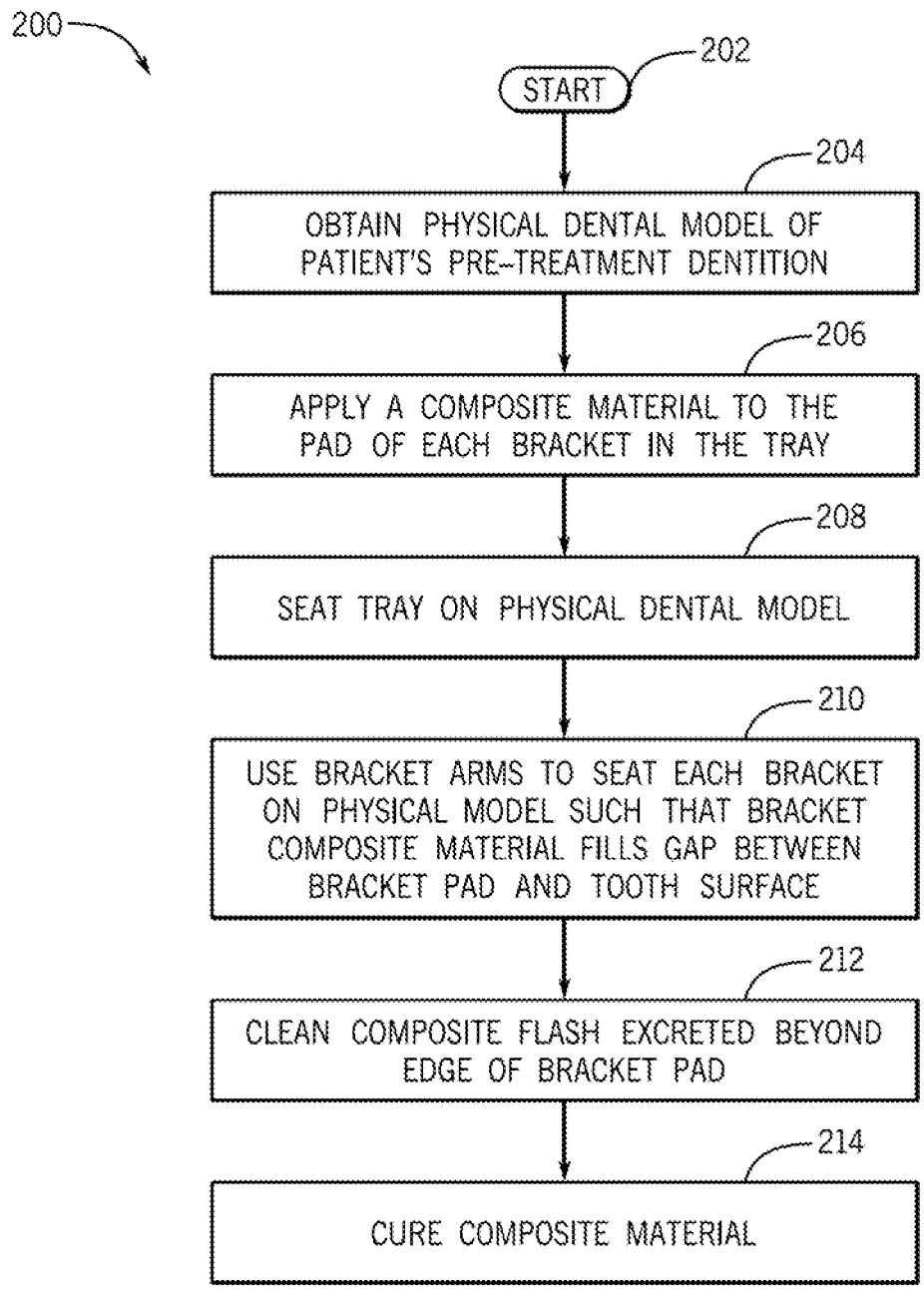
FIG. 9 is a flow chart that depicts a further method using an indirect bonding tray to construct customized composite bases to individualize brackets to a patient.

FIG. 9 is a flow chart that depicts an embodiment of a method 200 that may be formed in conjunction with the method 100 shown in FIG. 8 in order to provide an indirect bonding tray with brackets that have custom composite bases. In the method 200 the indirect bonding tray with attached brackets as from reference 120 in the method 100 of FIG. 8 are used at 202 to begin the method 200. At 204 a physical dental model of patient's pre-treatment dentition is obtained. As described above, in some embodiments, a physical dental model may be a plaster or composite material cast of the patient's pre-treatment dentition, and may be the same model that was scanned in step 102 in order to obtain a 3-D digital model of the patient's dentition. In an alternative embodiment, the physical dental model obtained at 204 may be a new model obtained if later it is determined that individualized composite bases are to be created for the patient.

At 206 the indirect bonding tray with the attached brackets as produced according to the method 100 (FIG. 8) is used and a composite material is applied to the pad of each bracket in the indirect bonding tray. In embodiments, the composite material may be selected from a variety of available dental composite materials, including, but not limited to, (UV) light curing, chemical curing, or thermal curing materials. The indirect bonding tray is seated on the physical dental model at 208.

Next, at 210, the bracket arms of the indirect bonding tray are used to seat each bracket on the physical model such that the composite material fills the gaps between the bracket pads and the tooth surfaces on the physical model. It is to be recognized that in practical performance of this method, the physical dental model may be treated with a release agent, such that the composite material does not stick or adhere to the physical dental mode after curing of the composite material. At 212 any composite material that excretes beyond the edge of the bracket pad is cleaned or removed and the remaining composite material is cured at 214. Non-limiting examples of the curing process for the composite material may include a UV curing, chemical curing, or heat curing process depending upon the specific composite material used for the base.

After the custom composite material bases have been created and cured, two alternative options exist for providing the indirect bonding tray to an orthodontist. In one embodiment, the composite bases are released from the physical model of the patient's pre-treatment dentition and the bracket arms are rotated into the first position such that the indirect bonding tray as described herein can be provided to an orthodontist with the custom composite bases.

In an alternative embodiment, the bracket arms are disconnected from the brackets and the brackets with the custom composite bases are left on the physical dental model of the patient's pre-treatment dentition. The indirect bonding tray, including the bracket arms, is removed from the physical dental model. Next, a conventional indirect bonding tray, such as one formed from silicone or other polymeric material which exemplarily may be formed by a vacuum molding process is formed around the physical dental model and the brackets with the custom composite bases. The conventional indirect bonding tray is then removed from the physical dental model with the encapsulated brackets with custom composite bases and the conventional indirect bonding tray with the custom composite bases is provided to the orthodontist.

Embodiments of the indirect bonding tray and methods as disclosed herein improve upon previous indirect bonding techniques. Ideal bracket placement is determined digitally and a custom, patient specific, indirect bonding tray with movable bracket placement arms is produced to ensure that the brackets are placed on the patient's teeth at the previously determined ideal bracket placements. The disclosed bracket arms allow the brackets to be precisely and repeatedly positioned at the digitally determined ideal bracket placement with or without custom composite bases on the bracket pad. Embodiments that include computer controlled custom composite bases on the bracket pads further individualize the fit of the bracket to each tooth surface in the patient's dentition.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An indirect bonding tray for use in the positioning of orthodontic brackets, the indirect bonding tray comprising:
    a tray comprising a plurality of interconnected tooth portions, each tooth portion of the plurality of interconnected tooth portions comprising an occlusal surface that conforms to an occlusal surface of an associated tooth of a patient's dentition;
    a plurality of bracket arms, each bracket arm of the plurality comprises a bracket arm tip adapted to engage an orthodontic bracket and movably engages a tooth portion of the plurality of interconnected tooth portions, each bracket arm being movable between a first position and a second position relative to a bonding surface of the associated tooth, wherein in the first position the bracket arm tip is in a position away from the associated tooth and in the second position, the bracket arm is in a position configured to hold an orthodontic bracket in a predetermined treatment position relative to the bonding surface of the associated tooth, wherein the predetermined treatment position comprises at least one of a predetermined torque, tilt, and rotation of the bracket relative to the bonding surface of the associated tooth;
    wherein each bracket arm is digitally designed and individually dimensioned relative to the predetermined treatment position for each associated tooth, each bracket arm being dimensioned such as to hold an orthodontic bracket in the predetermined treatment position when the bracket arm is in the second position.

2. The indirect bonding tray of claim 1, wherein each tooth portion of the tray comprises a second surface configured to engage a surface of the associated tooth opposite the bonding surface.

3. The indirect bonding tray of claim 2, wherein each tooth portion of the tray further comprises a third surface configured to engage a portion of the bonding surface of the associated tooth, wherein the third surface is dimensioned such as to leave a portion of the bonding surface of the associated tooth unobstructed to receive an orthodontic bracket.

4. The indirect bonding tray of claim 1, further comprising a stop associated with each tooth portion that mechanically defines the second position of the bracket arm associated with each tooth portion.

5. The indirect bonding tray of claim 4, wherein the stop is located on the bracket arm and engages the tray when the bracket arm is in the second position.

6. The indirect bonding tray of claim 4, wherein the stop is located on the tooth portion and engages the bracket arm when the bracket arm is in the second position.

7. The indirect bonding tray of claim 1, wherein each tooth portion further comprises a pivot pin, the bracket arm is pivotally attached to the pivot pin of each tooth portion, and the bracket arm moves pivotally about the pivot pin between the first position and the second position.

8. The indirect bonding tray of claim 1, wherein each tooth portion further comprises a guide that slidably receives the bracket arm and engagement between the bracket arm and the guide defines a movement path of a bracket arm between the first position and the second position.

9. The indirect bonding tray of claim 8, wherein each bracket arm further comprises a stop that engages the guide when the bracket arm is in the second position.

10. The indirect bonding tray of claim 1, wherein each tooth portion of the plurality of tooth portions is separable from an adjacent tooth portion of the plurality of tooth portions.

11. An indirect bonding tray for use in the positioning of orthodontic brackets, the indirect bonding tray comprising:
    a tray comprising a plurality of interconnected tooth portions, each tooth portion of the plurality of interconnected tooth portions comprising an occlusal surface that conforms to an occlusal surface of an associated tooth of a patient's dentition wherein each tooth portion of the plurality of tooth portions is separable from an adjacent tooth portion of the plurality of tooth portions and each tooth portion of the plurality of tooth portions comprises at least one tab and at least one slot, and a tab of a first tooth portion of the plurality of tooth portions removably engages the slot of a second tooth portion of the plurality of tooth portions;
    a plurality of bracket arms, each bracket arm of the plurality comprises a bracket arm tip adapted to engage an orthodontic bracket and movably engages a tooth portion of the plurality of interconnected tooth portions, each bracket arm being movable between a first position and a second position relative to a bonding surface of the associated tooth, wherein in the first position the bracket arm tip is in a position away from the associated tooth and in the second position, the bracket arm is in a position configured to hold an orthodontic bracket in a predetermined treatment position relative to the bonding surface of the associated tooth;
    wherein each bracket arm is digitally designed and individually dimensioned relative to the predetermined treatment position for each associated tooth, each bracket arm being dimensioned such as to hold an orthodontic bracket in the predetermined treatment position when the bracket arm is in the second position.

12. An indirect bonding tray for use in the positioning of orthodontic brackets, the indirect bonding tray comprising:
    a tray comprising a plurality of interconnected tooth portions, each tooth portion of the plurality of interconnected tooth portions comprising an occlusal surface that conforms to an occlusal surface of an associated tooth of a patient's dentition wherein each tooth portion of the plurality of tooth portions is separable from an adjacent tooth portion of the plurality of tooth portions and the tray comprises a plurality of perforations between each of the plurality of tooth portions;

a plurality of bracket arms, each bracket arm of the plurality comprises a bracket arm tip adapted to engage an orthodontic bracket and movably engages a tooth portion of the plurality of interconnected tooth portions, each bracket arm being movable between a first position and a second position relative to a bonding surface of the associated tooth, wherein in the first position the bracket arm tip is in a position away from the associated tooth and in the second position, the bracket arm is in a position configured to hold an orthodontic bracket in a predetermined treatment position relative to the bonding surface of the associated tooth;

wherein each bracket arm is digitally designed and individually dimensioned relative to the predetermined treatment position for each associated tooth, each bracket arm being dimensioned such as to hold an orthodontic bracket in the predetermined treatment position when the bracket arm is in the second position.

13. An indirect bonding tray system for positioning at least one orthodontic bracket, the indirect bonding tray comprising:

a first tooth portion comprising an occlusal surface that conforms to an occlusal surface of a first specific tooth of a patient's dentition and comprising a second surface that conforms to a surface of the first specific tooth opposite a bonding surface of the first specific tooth;

a first orthodontic bracket;

a first bracket arm comprising a bracket arm tip configured to engage the first orthodontic bracket, the first bracket arm movably attached to the first tooth portion to move between a first position and a second position wherein the first bracket arm is digitally designed relative to a predetermined idealized bracket placement for the first specific tooth such that the first bracket arm is dimensioned to hold the first orthodontic bracket in the predetermined idealized bracket placement relative to the bonding surface of the first specific tooth when the first bracket arm is in the second position, wherein the predetermined idealized bracket placement for the first specific tooth comprises at least one of a torque, tilt, and rotation of the first bracket relative to the first specific tooth;

a second tooth portion removably secured to the first tooth portion, the second tooth portion comprising an occlusal surface that conforms to an occlusal surface of a second specific tooth of the patient's dentition and comprising a second surface that conforms to a surface of the second specific tooth opposite a bonding surface of the second specific tooth;

a second orthodontic bracket; and a second bracket arm comprising a bracket arm tip configured to engage the second orthodontic bracket, the second bracket arm movably attached to the second tooth portion to move between a first position and a second position, wherein the second bracket arm is digitally designed relative to a predetermined idealized bracket placement for the second specific tooth such that the second bracket arm is dimensioned to hold the second orthodontic bracket in the predetermined idealized bracket placement relative to the bonding surface of the second specific tooth when the second bracket arm is in the second position, wherein the predetermined idealized bracket placement for the second specific tooth comprises at least one of a torque, tilt, and rotation of the second bracket relative to the second specific tooth.

14. The indirect bonding tray system of claim 13 wherein the first tooth portion is unitary with the second tooth portion and the first tooth portion is separated from the second tooth portion by a plurality of perforations.

15. The indirect bonding tray system of claim 13 wherein the first tooth portion comprises at least one tab and the second tooth portion comprises at least one slot, the first tooth portion removably secured to the second tooth portion by mating engagement between the at least one tab and the at least one slot.

16. An indirect bonding tray for use in the positioning of orthodontic brackets, the indirect bonding tray comprising:

a tray comprising a plurality of interconnected tooth portions, each tooth portion of the plurality of interconnected tooth portions comprising a pivot pin and an occlusal surface that conforms to an occlusal surface of an associated tooth of a patient's dentition;

a plurality of bracket arms, each bracket arm of the plurality comprises a bracket arm tip adapted to engage an orthodontic bracket and is pivotally attached to the pivot pin of a tooth portion of the plurality of interconnected tooth portions, each bracket arm moves pivotally about the pivot pin between a first position and a second position relative to a bonding surface of the associated tooth, wherein in the first position the bracket arm tip is in a position away from the associated tooth and in the second position, the bracket arm is in a position configured to hold an orthodontic bracket in a predetermined treatment position relative to the bonding surface of the associated tooth;

wherein each bracket arm is digitally designed and individually dimensioned relative to the predetermined treatment position for each associated tooth, each bracket arm being dimensioned such as to hold an orthodontic bracket in the predetermined treatment position when the bracket arm is in the second position.

17. The indirect bonding tray of claim 16, wherein each bracket arm is removably attached to the pivot pin of each tooth portion.

18. An indirect bonding tray for use in the positioning of orthodontic brackets, the indirect bonding tray comprising:

a tray comprising a plurality of interconnected tooth portions, each tooth portion of the plurality of interconnected tooth portions comprising a guide and an occlusal surface that conforms to an occlusal surface of an associated tooth of a patient's dentition;

a plurality of bracket arms, each bracket arm of the plurality comprises a bracket arm tip adapted to engage an orthodontic bracket and is slidably received within the guide of a tooth portion of the plurality of interconnected tooth portions, each bracket arm being movable between a first position and a second position relative to a bonding surface of the associated tooth, an engagement between the bracket arm and the guide defines a movement path of the bracket arm between the first position and the second position, wherein in the first position the bracket arm tip is in a position away from the associated tooth and in the second position, the bracket arm is in a position configured to hold an orthodontic bracket in a predetermined treatment position relative to the bonding surface of the associated tooth;

wherein each bracket arm is digitally designed and individually dimensioned relative to the predetermined treatment position for each associated tooth, each bracket arm being dimensioned such as to hold an orthodontic bracket in the predetermined treatment position when the bracket arm is in the second position.

19. The indirect bonding tray of claim 18, wherein each bracket arm further comprises a stop that engages the guide when the bracket arm is in the second position.

20. The indirect bonding tray of claim 18, further comprising a plurality of locking pins that each mechanically engage between a bracket arm of the plurality of bracket arms and a tooth portion of the plurality of tooth portions and lock each of the bracket arms in the second position.

* * * * *